United States Patent
Stone et al.

[19]

[11] Patent Number: 6,045,513

[45] Date of Patent: Apr. 4, 2000

[54] IMPLANTABLE MEDICAL DEVICE FOR TRACKING PATIENT FUNCTIONAL STATUS

[75] Inventors: Karen A. Stone, White Bear Lake; Vasant Padmanabhan, Plymouth, both of Minn.

[73] Assignee: Medtronic, Inc., Minneapolis, Minn.

[21] Appl. No.: 09/078,221

[22] Filed: May 13, 1998

[51] Int. Cl.[7] .................................................. A61B 5/02
[52] U.S. Cl. .............................................................. 600/508
[58] Field of Search ............................................. 600/508

[56] References Cited

U.S. PATENT DOCUMENTS

| | | | |
|---|---|---|---|
| 4,112,936 | 9/1978 | Schulman et al. | 600/595 |
| 4,353,375 | 10/1982 | Colburn et al. | 128/782 |

FOREIGN PATENT DOCUMENTS

| | | | |
|---|---|---|---|
| 0 472 411 A1 | 2/1992 | European Pat. Off. | A61B 5/07 |
| 0 535 508 A1 | 4/1993 | European Pat. Off. | A61B 5/11 |
| WO 94/05371 | 3/1994 | WIPO | A61N 1/37 |
| WO 97/24027 | 7/1997 | WIPO | A01K 11/00 |

*Primary Examiner*—W. Kamm
*Attorney, Agent, or Firm*—Harold R. Patton; Reed A. Duthler

[57] ABSTRACT

An implantable medical device determines activity levels over a set of time periods, preferably on the order of seconds, minutes and hours and a display is enabled for days or weeks at recorded activity levels over a range of dates. This enables physician review of patient functional status. Additional physiologic data can be recorded along with the activity data, and this too may be reported out from the implanted device to a medical communications system for alarm purposes, titrating drugs or other monitoring tasks.

23 Claims, 4 Drawing Sheets

IMPLANTABLE MEDICAL DEVICE FOR TRACKING PATIENT FUNCTIONAL STATUS

COPYRIGHT NOTICE

Except for the right to reproduce copies of this patent document, the use of all copyrightable material herein for any purpose whatever is expressly retained by the owners of this patent. Copyright Medtronic Inc., 1998, all other rights reserved.

This invention relates to the field of implantable medical devices for enabling enhanced medical monitoring of patients, most particularly for use with activity sensing, and has application to the field of monitoring patients generally and particularly those with conditions such as Cardiac Heart Failure (CHF).

BACKGROUND

There are numerous devices both implantable and external that have been used to monitor various medical patient conditions. Well known for heart patients is the Holter monitor which permits somewhat uncomfortable monitoring of an electrocardiogram for 24 hours which can then be read by a physician to find anamolies in the rhythm which were not susceptible to discovery or confirmation in a patient's office visit to the doctor. A number of other devices have improved on the ability to maintain records of electrocardiograms and numerous other health related patient parameters and even device performance parameters. Implantable medical devices such as pacemakers and cardioverter-defibrillators and even non-therapeutic monitoring devices are currently capable of maintaining some records and reporting out such data. An example of a non-therapy delivering monitoring implantable medical device can be seen in U.S. Pat. Nos. 5,313,953 and 5,411,031 issued to Yomtov et al., and in Holsbach et al, 5,312,446, and others. Nolan et al,'s U.S. Pat. No. 5,404,877 teaches that such devices can even generate patient alarms. All these patents are incorporated herein by this reference in that they provide information about what can currently be done in the implantable device field.

Current generation pacemakers and implantable defibrillators/cardioverters have the ability to store different types of information in order to provide feedback to the clinician about the patient/device system. Examples of stored information include arrhythmia diagnostics, histograms of paced and sensed events, electrograms and trends of lead impedance. Such information is useful not only in optimizing device programming but also in the management of the patient's arrhythmias and other conditions. While our invention focuses on the monitoring of patient activity, which we use as a functional status monitor, the additional information available from implantable devices could be used as an adjunct.

However, to date the literature is devoid of a satisfactory description of how to use activity information. There has been considerable thinking in this area, but none have yet succeeded in producing a satisfactory measure to track patient functional status. Some examples of this thinking in the current literature include:

Walsh J. T., Charlesworth A., Andrews R., Hawkins M., and Cowley A. J. "Relation of daily activity levels in patients with chronic heart failure to long-term prognosis", Am J Cardiol, 1997, 79: 1364–1369.

Rankin S. L., Brifa T. G., Morton A. R., and Hung J., "A specific activity questionnaire to measure the functional capacity of cardiac patients", Am J Cardiol 1996, 77: 1220–1223.

Davies S. W., Jordan S. L., and Lipkin D. P., "Use of limb movement sensors as indicators of the level of everyday physical activity in chronic congestive heart failure", Am J Cardiol 1992, 67: 1581–1586.

Hoodless D. J., Stainer K., Savic N., Batin P., Hawkins M. and Cowley A. J., "Reduced customary activity in chronic heart failure: assessment with a new shoe-mounted pedometer", International Journal of Cardiology, 1994, 43: 39–42.

Alt E., Matula M., Theres H., Heinz M. and Baker R., "The basis for activity controlled rate variable cardiac pacemakers: An analysis of mechanical forces on the human body induced by exercise and environment", PACE, vol 12, October 1989.

Lau C. P., Mehta D., Toff W. D., Stott R. J., Ward D. E. and Camm A. J., "Limitations of rate response of an activity sensing rate responsive pacemaker to different forms of activity", PACE, vol. 11, February 1988, and Lau C. P., Stott J. R. R., Zetlin M. B., Ward A. J., and Canim A. J., "Selective vibration sensing: a new concept for activity-sensing rate-responsive pacing", PACE, vol. 11, September, 1988. Matula M., Schlegl M., and Alt E., "Activity controlled cardiac pacemakers during stairwalking: A comparison of accelerometer with vibration guided devices and with sinus rate", PACE, 1996, vol 19, 1036:1041.

Specific Information Uses

The ability to perform normal daily activities is an important indicator of a patient's functional status and is related to improved quality of life in patients. An increase in the ability to perform activities of daily living (ADL) is an indicator of improving health and functional status, while a decrease in the ability to perform daily activities may be an important indicator of worsening health. Activities of daily living are submaximal activities performed during daily life. Examples are going to work, cleaning the house, vacuuming the house, cooking and cleaning, working in the garden, short walk to grocery stores, cleaning the car, and slow paced evening walks.

In order the assess the amount of daily activities that patients can perform and the ease with which they can perform these activities, clinicians typically ask their patients during office visits the following questions:

How do you feel?

Are you as active today as you were 2 months ago?

Are you as active today as you were 6 months ago?

Are you able to climb stairs?

How far can you walk?

Do you do your own grocery shopping?

Do you perform chores around the house?

Are you able to complete your activities without resting?

They also employ other tools such as the symptom based treadmill exercise test, the 6 minute walk test, questions and answers (Q&A), and quality of life(QOL) questionnaires in order to learn about their patients' ability to perform exercise and normal activities, but these assessment tools have limitations. Q&A techniques are subjective and biased towards recent events(at least partly due to patient bias toward present recall, if not also due to patient memory impairment or insufficiency, or a patient's desire to provide positive data). Maximal treadmill exercise tests assesses the patient's ability to perform intense (maximal) exercises and do not reflect the ability to perform normal daily activities.

The 6 minute walk test has to be administered very carefully and rigorously to achieve valid results.

Impairment of functional status can be seen in changes in the ability to perform exercises and ADL. This can be affected by many physiological factors such as progressive decompensation in the setting of left ventricular cardiac (LV) dysfunction, beta blocker treatment, symptomatic arrhythmias, and depression. These changes may take place over a long period of time and may be too subtle to be discerned by patients.

Physicians use answers to these questions and observation in clinic to determine what New York Heart Association "class" into which a patient falls, and on this basis, among others, they administer and alter treatment. Class I is defined as "Patients with cardiac disease but without resulting limitation of physical activity. Ordinary physical activity does not cause undue fatigue, palpitation, dyspnea or anginal pain." NYHA Class II is "Patients with cardiac disease resulting in slight limitation of physical activity. They are comfortable at rest. Ordinary physical activity results in fatigue, palpitation, dyspnea or anginal pain.", Class III is defined: "Patients with marked limitation of physical activity. They are comfortable at rest. Less than ordinary activity causes fatigue, palpitation, dyspnea, or anginal pain. And, Class IV is "Patients with cardiac disease resulting in inability to carry on any physical activity without discomfort. Symptoms of heart failure or of the anginal syndrome may be present even at rest. If any physical activity is undertaken, discomfort is increased."

As implantable device technology advances, there is a further need to provide information that will allow the clinician to not only manage arrhythmias better but also the progression of other diseases (co-morbidities) that patients may have. With the advent of newer drugs and newer paradigms in drug therapy (the use of beta blockers in heart failure patients is just one example), there is a need for objective measures of patient response. Several parameters such as ventricular pressure, patient activity, lung wetness, and heart rate variability may provide such information to the clinician.

In the management of patient care over a relatively long period of time, it is believed that current implantable devices with their larger memories and even using some extant sensors may be enhanced to produce a set of data that indicates patient functional status on an on-going basis. For patients who do not have already a need for an implanted medical device as an adjunct to their medical therapy, the addition of a specialized implantable that has extremely limited capability and thus small size may provide an additional tool for medical management of disease, particularly Cardiac Heart Failure (CHF).

However, it seems that the simplest and possibly most accurate measurement which can determine the prognosis and progress of a patient has not been previously monitored, and further this indicator has not been monitored in a manner effective to elucidate for the physician the changing character of the patient's CHF disease progression.

If there were a simple and yet effective measure that could be reliably correlated with the progress of CHF, the use of other hemodynamic measures could be used to supplement it and could easily be added to an implantable device. This indication alone may provide a sufficient justification for implantation of a device. In other words, if a very inexpensive implantable device could be developed to chronically monitor a simple indicator of CHF prognosis, the care available to CHF patients could be improved by using this data. Administration of patient care based on this inexpensive implant's data would improve the lives of CHF patients by virtue of their needing less frequent clinic visits for drug titration and other observationally intense activities, since the status of the patient could be determined without resort to an expensive doctor visit by merely and viewing the data from these CHF status indicators, the drugs themselves could be adjusted, alarms could be sent, and other therapies automatically adjusted based on this status report. It is believed that the common usage of such systems awaits the development of an information resource such as is taught in this patent.

We have determined that a long term trend of physical activity in CHF patients may thus provide the clinician with an objective measure of the patient's life-style and functional status, and can be used in conjunction with other information, but as explained previously, an objective long term measure is currently unavailable from implantable medical devices. Having available a display of a trend of patient ability to perform ADL is useful in several situations.

Correlation of Physical Activity with Patient Testimony

Clinicians often encounter patients who find it difficult to verbalize their symptoms clearly. In such situations, an objective measure of patient activity stored in the device may help the clinician to decide an appropriate course of action. For example, if a patient complains vaguely of fatigue and shortness of breath and is not able to describe the limitations to his/her daily activities, a trend of activities may help the clinician. If the activity data could show a considerable decrease in patient activities, then the clinician may take the next step such as the evaluation of cardiac profile, pulmonary dysfunction, or existing drug therapy. On the other hand, if the long term trend of activity in this patient is consistently regular, (i.e., no decrease in patient activity), the clinician may take alternative steps to understand the difference between patient symptoms and device indicated activity data.

Clinicians may also encounter situations when patients are reluctant to discuss their symptoms. In situations such as these, a trend of activity data may help the clinician to question the patient or the patient's spouse and enable the patient to come forward with their symptoms.

Correlation of Physical Activity with Onset or Progression of Heart Failure

Heart Failure is a syndrome characterized by the coexistence of left ventricular dysfunction (low EF), arrhythmias, pulmonary and peripheral congestion, and symptoms of fatigue and shortness breath. A majority of ICD patients have low EF (<40%) and decreased functional capacity (NYHA Class II, III and IV), and are at risk of developing heart failure. Clinical heart failure is a progressive disease; hence early identification and timely therapy may prevent hospitalizations, reduce the cost of care and improve patient lives.

In the earlier stages of heart failure, patients may not be able to perform strenuous activities and in the later stages, may not be able to perform even routine activities such as walking up a flight of stairs. Further, the inability to perform exercise and activities develop over a long period of time and hence may be difficult to discern and quantify. An objective measure of long term trends of patient activity may be useful in early identification of symptoms of heart failure and in the progression of heart failure. A gradual decrease in patient activities over the last 8 months may lead the clinician to suspect the development of heart failure. This may lead the clinician to take the next step in differential diagnosis.

The ability to perform daily activities is of particular relevance to the onset and progression of heart failure.

Several studies in the literature have described the need for an objective measurement of activities of daily living in patients with heart failure. This is no doubt why the NYHA measures focus so much on this ability to perform daily activities.

Correlation of Physical Activity with Patient Response to Therapy

The use of beta-blockers in patients at risk of arrhythmias or heart failure is becoming common clinical practice. Beta-blocking agents are known to blunt the heart rate response, which may affect the patient's ability to perform certain activities. The optimal dosage of beta-blocking agents is difficult to predict and may require trial and error methods. Further, there is usually a 30–60 day time period immediately after initiation of drug therapy during which the patient may not be very active. Most patients acclimate to the therapy after this period, but some don't. By having an objective measurement of patient activities, the titration and adjustment to beta blockers and other drugs could be enhanced.

Correlation of Physical Activity with Arrhythmias

Arrhythmias may cause symptoms such as palpitations, fatigue, or presyncope. Some patients may spend a significant amount of time in arrhythmias such as atrial fibrillation and may not be able to perform daily activities. Such issues can be coordinated with measurements of activity for increased diagnostic value.

As is known in the art, implantable medical devices exist that have various accelerometers and piezocrystal activity sensors and the like which count the movement of the crystal or sensor with respect to a resting state. Medtronic brand implantable medical devices with piezoelectric crystal or accelerometer based activity sensors have the ability to convert a raw activity signal into the 2 second activity counts. In other words, the number of times the accelerometer or sensor moves in a two second period is called a 2 second activity count. However, nothing in the art describes a method or apparatus for succinctly and effectively compiling such data as activity counts to make that data effective to solve the problems in diagnosis and patient tracking described above.

What is needed is a device with a system to convert these activity counts or some equivalent of them into a measure of patient activity that is clinically meaningful. To review the specifics of the problem consider the raw signal. The raw activity signal and hence the processed activity counts is a result of vibrations due to body movement. Activities such as walking and running cause body movement and vibration; the faster or longer the walk, more the vibrations, and larger the activity signal. Even though the raw activity signal is a good measure of activities such as walking and running, these raw counts, without our invention do not provide an accurate assessment of patient physical exertion. This is for three classes of reasons.

1. Body Vibrations are not Always Proportional to Level of Exertion

Any activity that causes body movement such as walking and running will generate an activity signal. Studies have shown that the amplitude of the activity counts increases in a linear fashion for walking activities. However, this linear relationship between intensity of activity and the activity signal during walking does not apply to all activities. For example, walking up-stairs at the same speed will produce activity counts similar to walking on a flat surface even though the intensity of activity is higher while walking upstairs. Other examples are isometric exercise, stationary bike, and jogging in place. Since the activity counts are derived from this activity signal, they may not be an objective measure of patients' exertion levels for all types of activity. In fact even a simple activity such as walking may produce different activity counts depending on the human-ground interface, for example, walking on a carpeted surface versus an asphalt surface.

2. Lack of Specificity

Activities such as automobile driving that result in body vibrations but do not involve exertion may sometimes produce an activity signal that may be comparable in amplitude to the level of the activity signal during walking. Likewise, the orientation of an accelerometer may not pick up an activity like push ups, despite the large exertion.

3. Inter-person Variability

There is also inter-person variability for similar activities. Differing size and fat content of the patient body, as well as placement of the device in various locations and orientations will all contribute to this kind of variability.

Based on these considerations, it is clear that in order to convert the activity counts to a meaningful measure of patient activity, the system must 1. be sensitive enough to pick up low-level activities (activities of daily living) as well as high-level exertion activities, 2. minimize response to activities such as automobile driving, 3. be patient independent, i.e., it should not require a user programmable parameter and should 4. be easy to implement in an implantable device

SUMMARY OF THE INVENTION

This invention provides a patient activity monitor for chronic implant which provides well correlated evidence of the functional status of the patient with the implant. It does so by monitoring an activity signal related to the movement of the patient, and from this monitored movement determining a level of activity indication signal value.

Detailed Description of the Preferred Embodiments

Nearly any currently implanted medical devices could be adapted to employ the features of this invention provided only that such a device maintains either a direct and constant link with a memory device or has its own memory device and its own activity sensor, and that there is provided an appropriate processing circuit or program to enable the invention activity. Activity sensors are well known and have been employed in pacemaker type implantable medical devices for many years. A typical such device is seen in Strandberg's U.S. Pat. No. 4,886,064, and it is now common to see the basic activity sensor combined with alternative means for sensing activity such as minute ventilation as in U.S. Pat. No. 5,562,711, both of which are hereby incorporated by this reference in their entireties.

Figure 7:
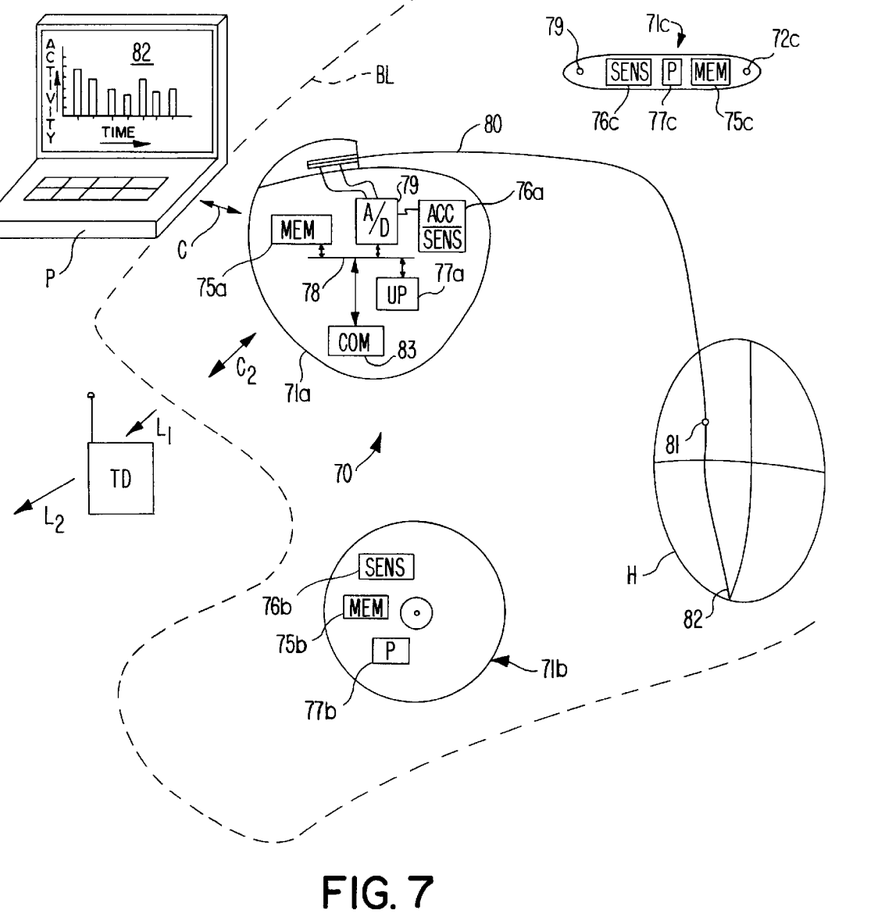
FIG. 7 is a drawing of the inside of a patient's body having three implants within it on the right side of a line BL and an external programmer for communication with the implantable devices.

Referring now to FIG. 7, in which a set of alternative implantable devices 71a–c are illustrated inside of a patient body, (the edge of which is here illustrated as line BL,) the typical application of this invention will be to provide data for a display 82 on an external device such as a programmer P external to the patient body, via a communications channel such as is here represented by double headed arrow C. The data may be shown in the form of a bar chart or line graph or similar display which indicates the total amount of some algorithmically derived measure of activity over a given period of time, such as a day or an hour. Device 71a is a pacemaker having a memory 75a which stores the data measured by the sensor 76a. The storage can be in a raw form if there is sufficient memory or it can be compressed in various advantageous forms by a program or other circuit device running a process such as processor 77a. In this embodiment, the microprocessor 77a runs a program stored in memory to convert sensed activity counts processed through an analog to digital converter 79 as they appear on a bus 78, and then returns the processed data to the program for temporary storage in the memory circuit 75a. When enough measurements are made in accord with the program, the microprocessor converts a representation of the total to a value and stores the representation in the memory. When an external device such as a programmer P requests a dump of these stored representations of value indicating the amount of patient activity over time, it is formatted and sent over the communications channel by a communications circuit 83 to the external device so that it can be displayed in a human readable form. Alternatively, of course, the data can be sent via communications here simply represented by arrow C2 and arrow L1 to be stored in a temporary device TD for later relaying to other devices by phone or othe rtelemetry, here represented simply by line L2, for later or contemporaneous but distant display. Only the simplest construction required for operative use of the invention is shown here. It is a simple matter to resend data over modern communications systems once it is retrieved in a machine readable format. As most implantable cardioverter defibrillators and pacemakers of today have microprocessors, memories and activity sensors, the addition of this invention to such devices would require no additional hardware, but mere software reconfiguration to accommodate the requirements of storing appropriate activity data in a useful manner so as a to be available for use in accord with this invention.

Also, alternative forms of implant devices can be used. The Medtronic device REVEAL(TM), for example is fully implantable and similar to the device illustrated as device 71c, with a memory and processing circuitry for storing electrocardiograms, taken across two electrodes 79 and 72c. The addition of an additional circuit for sensing activity and appropriate circuitry to implement the storage of the relevant activity data in an appropriate manner would make this type of device another good candidate for the inventive features herein described. Also a drug pump such as device 71b when outfitted with the appropriate memory, processing and sensing circuits (which are illustrated as within the sensor block 76b) could do the same, as could other currently implantable devices. It should be noted that a device with nothing but an activity sensor, memory, a processor and some form of communications circuit would also be sufficient to perform the tasks required of this invention's implantable device. By using a kinetic power source, the dependence on a battery could be eliminated too and the device could be extremely small and unobtrusive, permitting the clinician to easily obtain patient consent to accept the implant.

Once the valuable functional status data is available, any communications system could be employed to get the information to the doctor, or to update the patient file. Any such uses of the information provided by this invention are contemplated.

Figure 1:
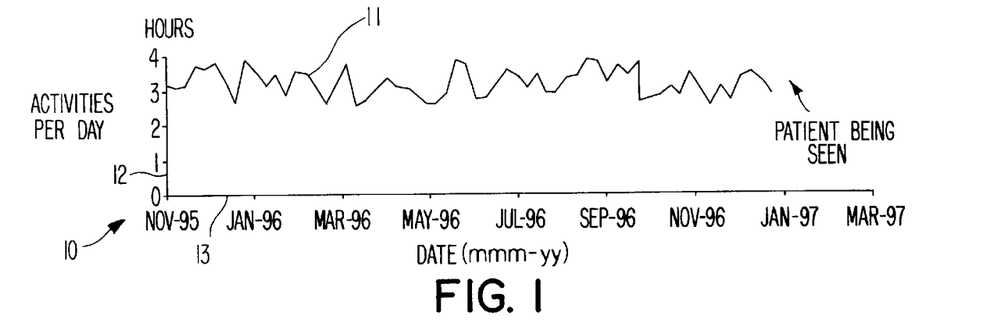
FIGS. 1–3 are graphs of time versus activity counts over time in accord with preferred embodiments of the invention, used to describe various changes in patient condition over time.
Figure 2:
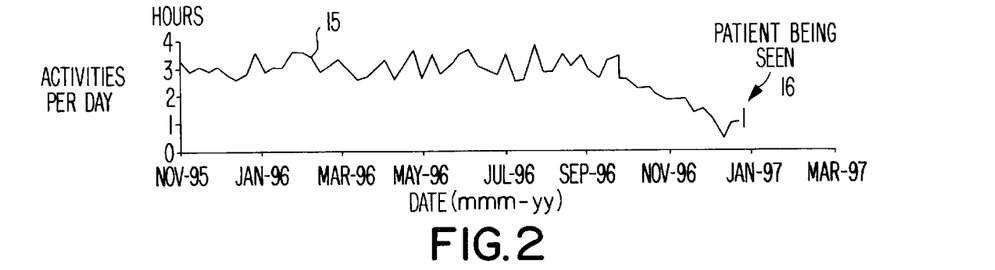

FIG. 1 is a prototype illustration (using simulated data) over a 14 month period of patient activity data. Note that the patient can be seen over a very long period and any changes in the activity amount will be readily visible. Also, as illustrated here, even fairly large variations in daily activity will not influence the overall impression of health. Here the graph 10 displays hours in which the activity count was in the active range per day 12 versus time 13 on the line 11. In FIG. 2, the activity line 15 begins trending downward in late September confirming that the patient should be seen at the time shown 16.

Figure 3:
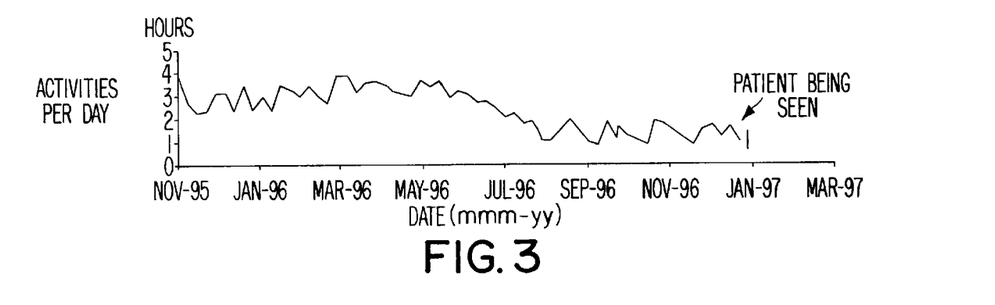

FIG. 3 illustrates a long term trend of patient activity data. This situation may be that of a post myocardial infarction (MI), sudden cardiac death survivor with EF<40%.

Figure 4A:
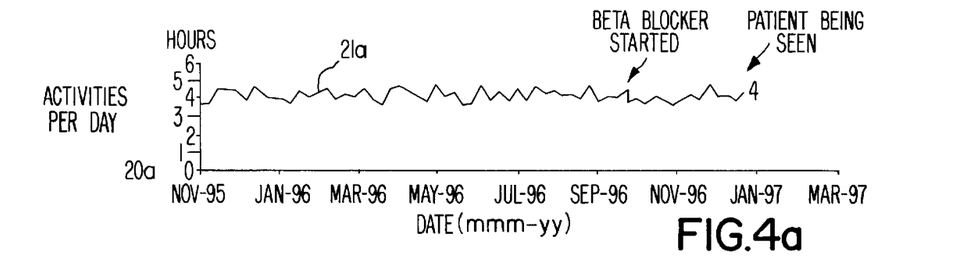
FIGS. 4a–c are similar graphs of activity versus time.
Figure 4B:
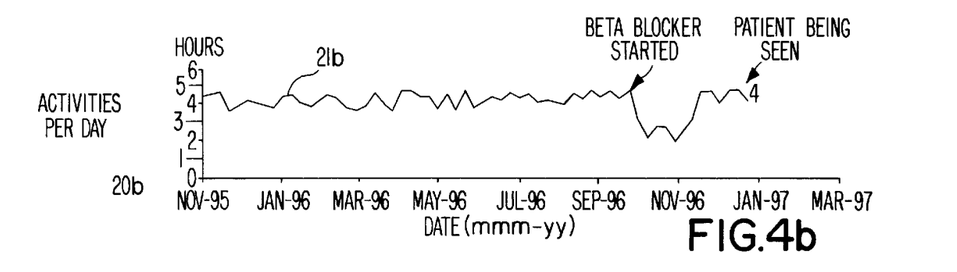
Figure 4C:
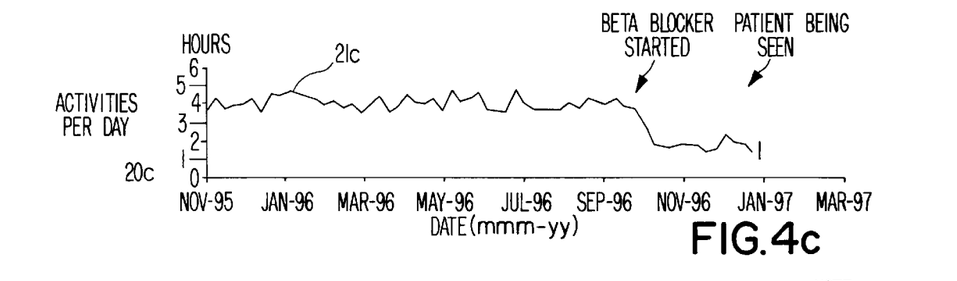

In the FIGS. 4a–c are prototypical illustrated activity trends for patients with a drug therapy intervention. In case 1, FIG. 4a, graph 20a, line 21a shown little or no effect of the drug regimen, the patient report at the time he is seen will probably indicate no change in status, based on the height of curve 21a. In case 20b, the drug administration has an apparent effect by the time the patient is seen, which in graph 20c, the line 21c shown no effect of the Beta blocker administration. Thus, objective measurement of patient activities as illustrated in FIGS. 4a–c can provide feedback to the clinician during the use of beta blocker therapy. FIG. 4a is a scenario where activities are not decreased. FIG. 4b illustrates a temporary decrease in patient activities followed by an increase to the original level. FIG. 4c shows that patient activities decreased and stay decreased, and may require the modification to the drug dosage.

Figure 5A:
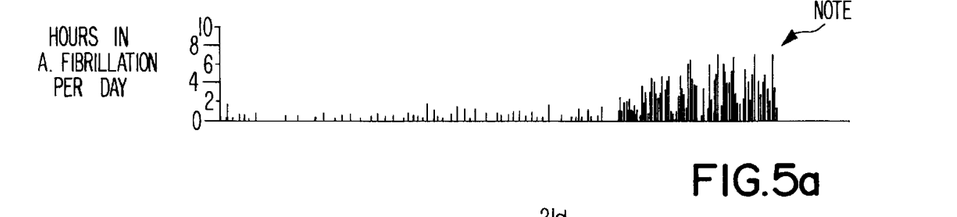
FIGS. 5a and 5b are graphs of atrial fibrillation versus time and activity versus time using the same time axis.
Figure 5B:
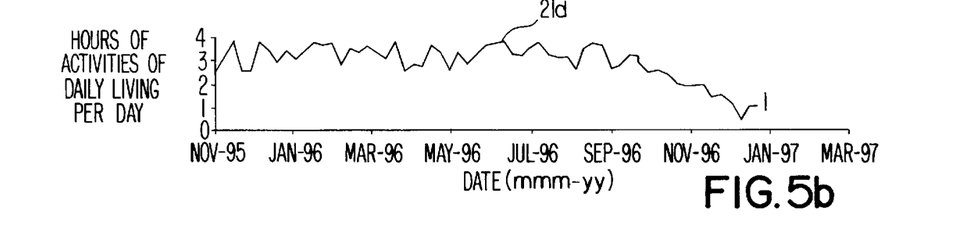

FIGS. 5a and 5b show how the activity data can be coordinated with a display of other patient related data, here hours in atrial fibrillation per day. Note the apparent correlation with the height of the line 21d and the increased occurrence of Atrial Fibrillation as would be expected. A device such as 71c which could track both fibrillation's and activity could be used to produce such a paired graph display. The ability to correlate the duration of arrhythmia episodes with patient activity as shown in FIG. 5 may help the physician in treating the arrhythmias. For example, if the patient is being monitored with a device that can display the occurrence of an arrhythmia or an accumulation of arrhythmic events over time as shown in this figure, or if such a feature is incorporated into the inventive device, the physician can learn immediately whether the arrhythmia occurs with activity, an important piece of diagnostic information.

Figure 6:
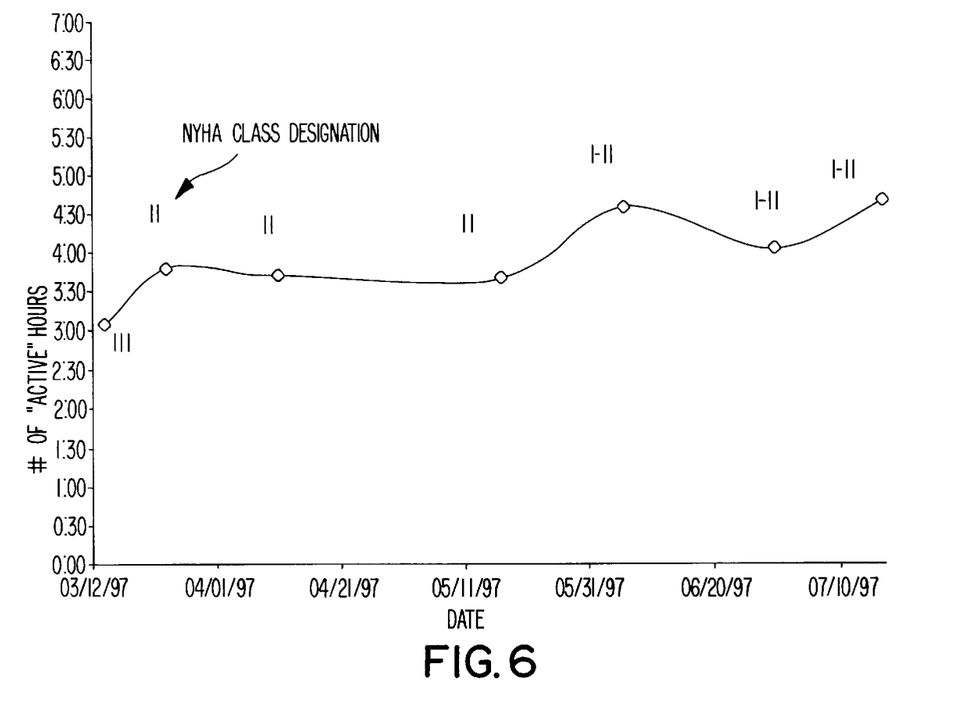
FIG. 6 is a graph indicating a NYHA class level with patient activity over time.

FIG. 6 illustrates correspondence with physician determined NYHA Class level of a CHF patient over a relatively short time period with his activity level in hours along the vertical axis. This chart shows the NYHA Classification and activities per day for the 7 follow-ups. As can be seen in the figure, activities per day appear to be increasing over time in correlation with the improvement in NYHA functional Classification from Class III to Class I/II.

In order to explain how the compilation of useful information from the raw data can be accomplished, refer first to FIG. 8 in which activity counts from a normal subject collected over a 24 hour period is shown.

These signals can be collected from pacemakers which have been using piezoelectric crystals and accelerometers mounted inside the pacemaker can as an indicator of patient activity to control the rate of the pacemaker. Typically, the raw accelerometer/crystal signal is first filtered using a bandpass filter and the total number of crossings above and below a fixed threshold is calculated every 2 seconds. The rate of the pacemaker is then calculated based on these 2 second activity counts. These 2 second activity counts can also be used to acquire information regarding patient activity. For heart rate and Heart Rate Variability(HRV), most pacemaker devices already have the ability to calculate heartbeat intervals and changes in these calculated variables over time gives the HRV. Other measures such as breathing rate, oxygen saturation, blood pressure, temperature, or just about any other measurement that can be made could be coordinated with the activity display to provide useful information, but we only show HRV here to teach that such can be easily done, not to limit the invention to this one coordination display. Thus we can have the additional sensors for measuring values of additional physiologic parameters (of a patient into which a device may be implanted) and we can produce measurement output therefrom, and process and store this additional physiologic data temporally related to the storage of the activity count data so as to be most useful in having a time coordinated set of data from the activity and other sensor(s), if any.

These observations are evidence that the concept of using the accelerometer signal to differentiate between activities and non-activities is appropriate and acceptable.

Description of Candidate Algorithms for Implementing this Invention

Based on the concerns just described we selected 5 candidate algorithms for determining a value for activity level per day, and we tested these on a large set of 24 hour data. A description of the 5 algorithms follow. These are examples only. We ultimately selected as a most preferred algorithm one which uses 60 second periods rather than 80, to provide easier conversion to minutes and hours. We also found that in producing a display it was sensible to average the daily values for a week, since normal activity cycles over a week can vary significantly over a weekend, particularly.

ADL1: First, the average activity count over 80 seconds is calculated by adding 40 consecutive 2 second counts. The average is then compared with a threshold of 1.5. If the average is greater than or equal to 1.5, then the 80s period is considered as activity (ADL), and the average for the next 80s time period is calculated. At the end of the 24 hour data, total activity duration is calculated by adding the number of 80 second windows that were detected as ADL, and multiplying with 80.

ADL2: This algorithm is similar to ADL1 except for the choice of threshold (2.0). This choice was made to evaluate the trade-off between detecting true ADL and driving, a lower threshold will detect most ADL as well as driving while a higher threshold will detect lesser driving and true ADL.

ADL3: This algorithm is similar to ADL2 except for the choice of window. Since we do not have any a priori knowledge of the typical duration of activities of daily living, a choice of 40 seconds was made in order to study the difference in performance between the 80 second and the 40 second windows.

ADL4: As described above, ADL1, ADL2 and ADL3 are threshold algorithms and do not attempt to separate out non-activities from activities based on variability (only amplitude information is used). In the ADL4 algorithm, the 80 second average is first calculated. The number of 2 second counts that are greater than 0 are also noted. If the 80 second average is greater than 1.0 and at least 16/40 2 second counts in the 80 second window are greater than 0, then the 80 second window is detected as ADL.

ADL5: This algorithm is another way to use the variability information. The 80 second window is separated into 20 second sub-windows and the average for the 80 second window as well as the 4 sub-windows are calculated. If the average of the 80 second window is greater than 1.0 and ¾ sub-window averages are greater than 0.3 *(average of 80 second window), then the 80 second window is detected as ADL.

Algorithm Evaluation

The 24 hour data set we used was collected from 10 normal subjects and separated into two groups, a Development data set and a Validation data set. Three performance measures P1, P2 and P3 were calculated for each data set in the Development data set. Algorithm parameters were adjusted to achieve the highest P1 and P2, and lowest P3. Since these performance measures are different from the traditional sensitivity and specificity measures used to evaluate algorithms, each of these measures is defined and explained below.

Performance Measure P1

P1=

Duration of marked ADL that is detected by algorithm)

Duration of marked ADL as marked by subject (gold standard)

We had the normal subjects mark those times they felt they were active. Upon close inspection of the marked ADL, it was found that several marked ADL events were of the stop-go-stop-go type, i.e., there were periods of rest in between short bouts of activity, which is characteristic of activities of daily living. In order not to penalize the algorithm for the detection of rest periods in between marked ADLs, only that part of marked ADL that was associated with an elevated heart rate (heart rate during rest period during day+10 bpm) was considered as marked ADL. This procedure can be thought of as refining the gold standard data.

Performance Measure P2

This measure was used to ascertain whether the algorithm was detecting non-activities as ADL. Since not all activities and non-activities are marked, a heart rate based criterion was used to differentiate between activities and non-activities. Specifically, activities that were associated with a elevated heart rate (resting heart rate during day+10 bpm).

P2=

Total time detected as ADL associated with a elevated heart rate (P2N)

Total time detected as ADL (P2D)

For example, to calculate P2 from a 24 hour data set, P2D is calculated as the # of 80 second activity windows detected as ADL by the algorithm. To calculate P2N, the heart rate in the 80 second window corresponding to the 80 second activity window that is detected as an ADL is calculated first. If the heart rate in this window is above (rest heart rate+10 bpm), then the 80 second activity window is said to be appropriately detected. The ratio of P2N and P2D is the performance measure P2.

Performance Measure P3

This measure is used to ascertain the ability of the algorithm to eliminate detection of automobile driving as ADL. Automobile driving (or riding in a bumpy conveyance of any type) we believe will be one of the main causes of false positives. This measure P3 is calculated as the ratio of P3N and P3D, where P3D is the total duration of marked driving by the normal subject and P3N is the duration during which marked driving was detected as ADL. Clearly, the lower P3 is, the better the algorithm.

P3=

Total driving time that is detected as ADL (P3N)

Total marked driving time (P3D)

Calculation of Heart Rate

To obtain heart rate data, 24 hour surface ECG data stored in a Holter Monitor system were downloaded and analyzed using "Holter for Windows"(TM) software (available through Rozin Electronics, Glendale N.Y.). Every beat of the ECG data (each beat corresponds to the detection of a QRS complex) was classified as a Normal beat, Ventricular beat, Supra-ventricular beat or an Artifact. Only intervals between normal (sinus) beats (referred to as NN intervals) were used to compute heart rates during the entire 24 hour period.

The accelerometer signal is processed and a raw count is calculated every 2 seconds (ACTCNT) for pacemaker rate response. An algorithm to calculate minutes of ADL from ACTCNT is as follows:

[Where NUM is the total number of activity counts, THRESH is the threshold for whether the activity count value will be counted as a one or a zero in the SUM of counts, and DAILYCOUNT is the variable value to be displayed for a single day. It should be noted that if the values of a week of DAILYCOUNTs are averaged to provide a single point to display as was the case for the graphs of FIGS. 1–5, the average value will be what is displayed, but for more detailed analysis, even if averaging is used, the DAILYCOUNT values would preferably be retained beyond a given week, unless the device in question is operating with minimal memory capacity.]

Step 1. Starting at 12 a.m. (00:00:00), add NUM ACTCNT, i.e., SUM=S ACTCNT/NUM.

Step 2. If SUM>THRESH, increment a counter (DAILYCOUNT) else next step.

Step 3. Repeat Step 1 and 2 continuously till the next 12 midnight

Step 4. Save DAILYCOUNT for this day and repeat Steps 1–4

If averaging over a larger period, average the DAILY COUNT values for the past number of days in the period and establish a larger value representing the average, AVDAILYCOUNT for the period, so that that value AVDAILYCOUNT can be displayed.

NUM and THRESH are 1 byte programmable

Recommended values are NUM=30, THRESH=45

Memory requirements

For NUM=30, DAILYCOUNT could have a maximum value of 1440 and would require 2 bytes of storage every day.

Total memory: 2 bytes a day (850 bytes for 425 days)

Software Algorithm and Printing

Step 1. ADLDAY=DAILYCOUNT * NUM * 2/60

Step 2. ADL=Avg. (7 consecutive ADLDAY)

Graph ADL every week as illustrated in "Long Term Clinical Trends"

Y axis title: "Total hours of patient activity per day"

Y axis tick labels: "0 2 4>6" Hours

Algorithm Evaluation

As detailed above, each of the 5 candidate algorithms were applied to each of the 5 data sets in the Development data set and the three performance measures P1, P2 and P3 calculated. The algorithm parameters were changed to maximize P1 and P2 and minimize P3. The values and brief descriptions of P1, P2 and P3 for each of these 5 normals is shown in Table 2. Following algorithm development, the algorithms were applied to the Validation data set and the process repeated. Table 3 shows the performance measures for the Validation data set. It is important to note that the utility of the performance measures is limited to the comparison of the different algorithms only and is not meant to be used as an absolute measure of sensitivity and specificity.

As detailed in the Methods section, each of the 5 candidate algorithms were applied to each of the 5 data sets in the Development data set and the three performance measures P1, P2 and P3 calculated. The algorithm parameters were changed to maximize P1 and P2 and minimize P3. The values and brief descriptions of P1, P2 and P3 for each of these 5 normals is shown in Table 2. Following algorithm development, the algorithms were applied to the Validation data set and the process repeated. Table 3 shows the performance measures for the Validation data set. It is important to note that the utility of the performance measures is limited to the comparison of the different algorithms only and is not meant to be used as an absolute measure of sensitivity and specificity.

TABLE 2

Performance measures for Development data set

| | P1 | P2 | P3 |
|---|---|---|---|
| ADL1 | 70% | 86% | 28% |
| ADL2 | 62% | 91% | 20% |
| ADL3 | 60% | 89% | 20% |
| ADL4 | 72% | 86% | 42% |
| ADL5 | 65% | 87% | 36% |

P1: Ability of the algorithm to detect marked ADL activities
P2: Abllity of the algorithm to detect activities that are associated with an increase in heart rate
P3: Ability of the algorithm to detect automobile driving.

TABLE 3

Performance measures for Validation data set

| | P1 | P2 | P3 |
|---|---|---|---|
| ADL1 | 72% | 80% | 24% |
| ADL2 | 66% | 85% | 14% |
| ADL3 | 63% | 84% | 14% |
| ADL4 | 74% | 80% | 36% |
| ADL5 | 66% | 80% | 28% |

Several observations can be made from these results. Given that the goal of the algorithm is to maximize P1 and P2 and minimize P3, it is clear from Table 3 that algorithm ADL1 and ADL2 best meet the criteria. The only difference between ADL1 and ADL2 is the threshold parameter, ADL1 had a threshold of 1.5 and ADL2 had a threshold of 2.0. It is to be expected that a higher threshold (ADL2) would lead to a decreased sensitivity (P1 is lower for ADL2) and but increased specificity (P2 is higher for ADL2). The only difference between ADL2 and ADL3 is the choice of window (ADL2 used a 80s window while ADL3 used a 40s window). Based on the results, it appears that decreasing the window from 80s to 40s had a minimal effect on the performance measures. This may be because most ADL may have been longer than 40 seconds. The variability algorithms do not appear to detect driving any less than the threshold type algorithms. This may be because of the fact that the variability of driving while evident in the 2 second data may not be a factor when data is averaged over 80 seconds. Table 3 shows the performance for the Validation data set. The results from the Validation data set are consistent with the observations made from the Development data set.

Based on these observations, ADL1 (essentially same as ADL2) algorithm was chosen as the algorithm of choice since this algorithm has the highest sensitivity for marked ADL activities. Coincidentally, this algorithm is associated with the least implementation complexity.

Comparison of ADL Between Normals and Heart Failure Patients

As explained in the Data Collection section, 24 hour activity and heart rate data were collected from 10 heart failure patients as part of the EXACT study in addition to the 10 normal subjects as part of the Normal study. Such data were collected 7 times from each patient over a period of 16 weeks. However, detailed diary data were not collected from the patients as was from the normal subjects. Even though the 24 hour EXACT data from the patients do not lend themselves to the type of analysis performed on the data from normal subjects, these data were used to study algorithm performance in two different ways.

Thirty (30) data sets, each consisting of 24 hour heart rate and activity data from a patient were analyzed using algorithm ADL1. At the beginning of the 24 hour follow-up, each patient undergoes a 10 minute rest period and a 6 minute walking test. Each of these two events are marked using the DR180 Holter apparatus. Based on these data 29/30 waking activities (6 minute walks) were detected successfully and none of the 30 rest periods were detected. The only activity episode not detected by the algorithm was the 6 minute walk from Patient 2, Baseline Evaluation. On closer inspection of the data, it was found that this patient was walking extremely slowly (40 steps per minute). However, the 6 minute walk from the same patient during her subsequent follow-ups were detected appropriately, because she walked faster than 40 steps per minute.

Another way of using the 24 hour data from heart failure patients is to compare the total ADL/per day from the heart failure patients with the normal subjects. FIG. 14 shows the daily activities (hours:minutes) for each of the 10 normal subjects and 30 data sets from heart failure patients, Mean ADL/day was 4 hours 51 minutes in Normal subjects and is significantly greater than ADL/day of 2 hours and 10 minutes of the heart failure patients. Even though this result is not unexpected (one would expect the normal subjects to be more active than the heart failure patients) and the normal subjects are not age matched, it does provide a "reality check" of the algorithm. In fact, one may argue that the ability to separate out normal subjects from heart failure subjects based on their activities is a desired attribute of an algorithm.

The General Approach

The algorithm accepts the filtered activity count for a two second interval. As mentioned previously, this is bandpassed data from a sensor such as an accelerometer that measures a count every time it moves. Various forms of activity sensor could be used which would require different pre processing. For example, if a three axis accelerometer were used, one could filter out or ignore the activity occurring outside of a particular plane of acceptable motion, such that a patient moving up and down would register a count, but one moving sideways may not. Alternatively only large excursions in signal output indicating a movement or shock of a sufficient size could be employed, thereby removing small movements form the calculation. If motion is detected from changes in a resonant microbeam sensor due to stress or pressure, different pre filtering schema must likewise be adopted. What is essential is that a mechanism be adopted to generate a count that gives a rough absolute value range for the amount of movement or change experienced by the sensor over a short period of time, and that this value then be averaged or otherwise compared to the other short period activity values collected over a larger period of time. In our preferred embodiment we used 2 seconds for the short period and one minute for the long period because of convenience, but any vaguely similar pair could be used, for examples, one second short over 2 minute long periods, or thirty second short over half hour long periods. One could even name the long periods to correspond to day times to produce a display color or three dimensions with values for the activity counts per hour displaying more toward the red side of a spectrum for higher activity and more toward the blue for less, or vice versa, thus providing a diurnal chart.

While all these variations and more will naturally occur to one of ordinary skill in this art, we have found it to be perfectly acceptable to use a single axis accelerometer or piezocrystal with a value of 1.5 counts per minute as reasonable for cardiac patients. The amount of activity of a cardiac patient will generally be quite low on average and we want to pick up even small activities in the case of the CHF patient. Our studies indicated that an activity level of a 95 steps per minute over the minutes walked of a healthy person was about 23, but at 60 steps per minute the average count was more like 5 or 8 counts per walked minute. Since the CHF patient will be doing few walks of more than a minute the expectation is that nearly all two second periods will register a zero activity signal, which was born out through experiment. However, it should be recognized that if the small period chosen is larger, or the activity sensor more sensitive than what we used, a larger count may be expected, possibly necessitating an adjustment in the exclusion level above what we chose as 1.5 average counts per minute period. Similar adjustments to this value will occur to the reader without the need for undue experimentation. So in general, in our preferred embodiment, to find the number of active 1 minute periods in a 24 hour period, a raw activity count is established for each two second period. To capture the patient in ADL, we use an average of 1.5 activity counts for each of the 2 second periods in a minute. Thus if the sum of activity counts in a minute, divided by the number of short periods is greater than 1.5, we declare the minute containing these short periods "active". We then do this for a 24 hour period and add up the active periods to get our chartable data point. We could use some other mathemetal function besides averaging, such as to pick the mean or maximum value, but these while possibly acceptable are less preferred. Many other well known mathematical functions could be used within the skill of the practitioner of this art to substitute for average if desired.

Therefore, in general, we are figuring on the basis of the number of short periods (like a 2 second interval), that a patient is determined to be active over the course of a first larger period, one can thus establish a clinically valuable data set of larger period activity that corresponds to the medically recognized functional status of the patient. In our preferred algorithms, we employed two period sizes larger than the first larger period just mentioned to refine the available data and produce an easily useable display. The period larger than the first larger period is a day, in our preferred embodiments. Thus the number of active first larger periods in a day can easily be tallied and displayed as a percentage or number of hours in the day period. In our most preferred embodiment, we average the value established each day over a week, which allows for what we believe to be more useful information to be displayed, since patient activity is normally quite variable over the course of a week and also so that a smaller display can be used for a large set of data.

Because this can be confusing, we use the following example for a detailed discussion of the application of the concept for a 2-second count set over a minute period.

EXAMPLE 1 cs=counts/2sec. period

If cs is an element of the set containing the count values for each 2 second period in a minute, i.e.,

{0,0,0,0,1,0,0,15,30,32,10,2,0,0,1,0,0,0,0,0,0,0,01,0,2,1, 0,0,0}, then the average value (the sum of the elements' values divided by the number 30), then the value for that minute is approximately 2.7, which is greater than the 1.5 we are using for the cut-off point, so a positive activity value gets recorded for this minute.

EXAMPLE 2 if cs=counts/2 second period and

If cs is an element of the set containing the count values for each 2 second period in a minute, i.e., {0,0,0,0,0,0,1,0, 0,0,1,0,0,1,5,3,2,0,0,0,0,2,8,0,0,0,0, 3,0,1,0,0},then the average value (the sum of the elements' values divided by the number 30), for that minute is less than 1 so a negative or zero activity attribute is stored for that minute.

Depending on the kind of display desired, we can telemeter or otherwise communicate the data from an implanted device monitoring activity data in the way we describe which includes any subset of the data or all of it. Preferably a display of the amount of activity in a day, averaged over a week will be displayed for a number of months in a display similar to the graphs illustrated in FIGS. 1–5. Additionally, this data can be printed out for storage and later use by reference to a patient's file.

Many adaptations can be made upon the information provided by this invention. For one thing, a patient alarm may be sounded to incent the patient to comply with an exercise regimen or to call his doctor. Today small and low power piezo speakers with small speech producing circuitry are plentiful and inexpensive. The data here if it shows a failure or inability of the patient to comply with an exercise regimen could actually speak to the patient and say things like, 'time to get on the treadmill' or 'time to go to the doctor' or something similar, based on the severity of the failure of the patient to achieve the activity goals set with his physician and programmed into the device. Additional patient signals like a buzzer, shaker, or even electric shock could be provided to get the patient's attention. As already mentioned, if a particular activity pattern is developing, and this device is included in a drug pump, the drugs the patient is receiving could be adjusted based on his activity level, the angle of its downward or upward slope, or other characteristics determinable based on this activity data set.

Also, if the device records arrhythmias sensed through auto triggering mechanisms or through patient activation of the event record we can report this data out with an indication of it's temporal correspondence to activity level. This can tell the physician whether the arrhytmia occurred during rest or activity. Arrhythmia monitoring background art, hereby incorporated by this reference includes U.S. Pat. Nos. 5,113,869; 5,313,953; and 5,086,772. Also incorporated by reference are the following patents on triggering recordings of arrhythmic events, both automatically and by patient activation; U.S. Pat. Nos. 4,086,916; 5,404,877 and 5,012,814.

Another less preferred embodiment would be to use an external device strapped or otherwise affixed to a patient's body to collect the activity data, (requiring of course some adjusment to the prederemined value for deciding whether a minute period qualified to be called active), but considering the difficulty in gaining patient compliance or comfort, we feel the implantable versions will be most efficatious.

Many variations on the teachings of this invention may fall within its ambit, but the invention is only limited by the following claims.

What is claimed is:

1. An implantable medical device useful for tracking patient functional status by displaying values upon which an evaluation of said functional status can be made, said implantable medical device comprising a housing having an activity sensor and circuitry therein for recording output from said activity sensor wherein said output is compressed in accord with a processing circuit constructed to operate a procedure to iteratively, after the expiry of each of a first size time interval:

add up via a summation means a number of activity counts sensed per a first one of each first time size intervals to produce a first sum, and if said first sum is greater than a predetermined value, storing a count value representing the result of comparing said first time size interval first sum to said predetermined value in a memory means, then to repeat this add up procedure for subsequent ones of said first time size intervals and to store a first time size interval count value for said first size time intervals occurring within a second size time interval in said memory means, then to determine via a computation means a first display value for a representation of said stored first time size interval count values, and storing said first display value representing a total value for said second time size interval.

2. A device as set forth in claim 1 further comprising means for providing said first display values to a display means for displaying a second display value wherein said second display value is a sum of said first display values.

3. A device as set forth in claim 1 wherein said implantable medical device has an alarm circuit which can function to become active based on checking an alarm flag value in a memory and wherein said processing circuit is adapted to operate said procedure to further iteratively determine if said first display value is a predetermined function of a predetermined alarm value, and for storing a result of said determination, and for setting said alarm flag value based on the result of said determination.

4. A device as set forth in claim 3 wherein further comprising a patient-alarm alarm interface which is activated when said alarm flag value equals a predetermined alarm flag activation value.

5. A device as set forth in claim 4 wherein said patient-alarm interface is an audible sound generator.

6. A device as set forth in clam 5 wherein said audible sound generator comprises speech generator means adapted to produce intelligible speech.

7. A device as set forth in claim 1 wherein said processing circuit is adapted to further determine if activity values represented by said first display values match a programmable pattern of activity level, and to set a flag indicating such a change.

8. A device as set forth in claim 1 wherein said housing further comprises additional sensor means for measuring values of additional physiologic parameters and producing measurement output therefrom, and wherein said processing circuit constructed to operate said procedure processes and stores in said memory, temporally related to said first display values, additional physiologic measurement values taken from said additional sensor means output.

9. A device as set forth in claim 8 wherein said additional sensors are appropriately adapted and disposed connection with and in relation to said housing and said circuitry to sense and to record in said memory, physiologic signals including any of those drawn from the set of possible sensor signals including arrhythmias, arrhythmias during rest periods, respiration rate during rest periods, respiration rate, occurrence of abnormal breathing episodes during rest, change in sinus rate during rest, heart rate variability, blood pressure, ST segment variation, blood oxygenation, and temperature.

10. A device as set forth in claim 1 wherein said housing further comprises additional sensor means for measuring values of additional physiologic parameters of a patient into which said device may be implanted and producing measurement output therefrom, and wherein said circuitry for processing and storing values processes and stores temporally related to said first display values, additional physiologic measurement values taken from said additional sensor means output.

11. A medical system, as set forth in any one of claims 1–7, 8, 9, or 10 further comprising a receiving device for receiving patient data from said implant including representations of said first display values having a communications link to a communications system to enable the communication of said representation of said first display values to a remote device for subsequent display.

12. An implantable medical device (IMD) comprising means for tracking activity counts generated by an activity sensor in said IMD over small units of time and means for storing a compilation of values related to combined sums of said activity counts for a sum of said small units of time over larger units of time and having means for detecting and for recording arrhythmic cardiac events such that said compilation of values is stored with an indication of temporal relatedness to any arrhythmic events which may be detected and recorded by said means for detecting and recording substantially contemporaneously with the storing of said compilation of values.

13. An implantable medical device having an activity crystal for determining a counts value for each "a" second period based on activity sensed by said activity crystal, a processing circuit for averaging each said counts value over the number of a second counts in each minute, and for generating an average counts value therefrom, and a memory circuit for storing a positive activity value for said average counts value for each minute if said average counts value is greater than a predetermined value.

14. An implantable medical device as set forth in claim 13 further comprising a processing circuit for storing a sum of all said positive activity values.

15. A device adapted for affixation to a patient for tracking patient functional status by producing display values upon which an evaluation of said functional status can be made, said device comprising a housing having an activity sensor and circuitry therein for recording output from said activity sensor wherein said output is compressed in accord with a processing circuit constructed to operate a procedure to iteratively, after the expiry of each of a first size time interval:
   add up via a summation means a number of activity counts sensed per a first one of each first size time intervals to produce a first sum, and if said first sum is greater than a predetermined value, storing a count value representing the result of comparing said first size time interval first sum to said predetermined value in a memory means,
   then to repeat this add up procedure for subsequent ones of said first size time intervals and to store a count value for said first size time intervals occurring within a second size time interval,
   then to determine via a computation means a first display value for a representation of said stored count values, and storing said first display value representing a total value for said second size time interval.

16. A method of tracking patient functional status by enabling a display upon which an evaluation of functional status can be made comprising:
   measuring activity counts with an implantable activity sensor,
   recording output from said activity sensor said output is compressed in accord with a procedure which iteratively, after the expiry of each of a first size time interval:
   adds up a number of activity counts sensed per a first one of each first time intervals to produce a first sum, and if said first sum is greater than a predetermined value, storing a count value representing the result of comparing said first time interval first sum to said predetermined value in a memory means,
   then repeating this add up procedure for subsequent ones of said first size intervals and storing a count value for said first size time intervals occurring within a second size time interval,
   then determining a first display value for a representation of said count values from said ad up procedure, and
   storing said first display value.

17. A method as set forth in claim 16 further comprising providing said first display values to a display means, then generating a second display value comprising a representation of a sum of said first display values for a diurnal time period, and then displaying said second display value.

18. A method as set forth in claim 16 comprising the additional steps of:
   (a) further iteratively determining if said first display value is a predetermined function of a predetermined alarm value,
   (b) storing a result of said determination, and,
   (c) then setting an alarm flag representing the result of said determination.

19. A method as set forth in claim 18 wherein if said alarm value flag is set, activating a patient alarm to notify the patient.

20. A method for displaying representations of said first display values generated by any of the methods as set forth in any one of claims 16 or 17–19, further comprising the step of receiving said first display values for generating a display, and adding up all the first display values for a diurnal period and displaying a visual representation of said value of said sum for each said diurnal period in a range of diurnal periods.

21. The method for displaying representations of said first display values generated by any of the methods as set forth in any one of claims 16 or 17, 19 further comprising the intermediate step of averaging all said diurnal period values for a week and then displaying a visual representation of the value of the week average for the week.

22. A method as set forth in claim 13 further comprising communication the first display values to an external device.

23. A method as set forth in claim 22 further comprising activating an alarm system in said external device wherein said alarm system sets a flag indicating a need to take corrective action if the display values received by said external device alarm system match a predetermined pattern.

* * * * *